United States Patent
Eisenacher et al.

(10) Patent No.: US 9,353,032 B2
(45) Date of Patent: May 31, 2016

(54) METHOD FOR THE PRODUCTION OF NEOPENTYL GLYCOL

(71) Applicant: Oxea GmbH, Oberhausen (DE)

(72) Inventors: Matthias Eisenacher, Wesel (DE); Kurt Schalapski, Oberhausen (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 14/427,181

(22) PCT Filed: Sep. 28, 2013

(86) PCT No.: PCT/EP2013/002922
§ 371 (c)(1),
(2) Date: Mar. 10, 2015

(87) PCT Pub. No.: WO2014/067600
PCT Pub. Date: May 8, 2014

(65) Prior Publication Data
US 2015/0239809 A1    Aug. 27, 2015

(30) Foreign Application Priority Data

Oct. 29, 2012 (DE) .......................... 10 2012 021 280

(51) Int. Cl.
| | | |
|---|---|---|
| *C07C 31/18* | (2006.01) | |
| *C07C 29/141* | (2006.01) | |
| *B01J 37/03* | (2006.01) | |
| *B01J 37/04* | (2006.01) | |
| *B01J 37/08* | (2006.01) | |
| *B01J 23/889* | (2006.01) | |
| *C07C 45/75* | (2006.01) | |

(52) U.S. Cl.
CPC ........... *C07C 29/141* (2013.01); *B01J 23/8892* (2013.01); *B01J 37/031* (2013.01); *B01J 37/04* (2013.01); *B01J 37/08* (2013.01); *C07C 45/75* (2013.01)

(58) Field of Classification Search
CPC ........................................................ C07C 31/18
USPC ........................................................... 568/852
See application file for complete search history.

(56) References Cited

U.S. PATENT DOCUMENTS

| | | | |
|---|---|---|---|
| 3,340,312 A | 9/1967 | Duke, Jr. et al. | |
| 4,250,337 A | 2/1981 | zur Hausen et al. | |
| 4,855,515 A * | 8/1989 | Morris ................. | C07C 29/141 568/862 |
| 8,357,824 B2 | 1/2013 | Schulz et al. | |

FOREIGN PATENT DOCUMENTS

| | | | |
|---|---|---|---|
| DE | 1518784 A1 | 8/1969 | |
| DE | 102008033163 A1 | 1/2010 | |
| EP | 0006460 A1 | 1/1980 | |
| EP | 0301853 A1 | 2/1989 | |
| EP | 0484800 A2 | 5/1992 | |
| EP | 0522368 A1 | 1/1993 | |
| GB | EP 0301853 A1 * | 2/1989 | ............. B01J 23/868 |
| GB | 2482887 A | 2/2012 | |
| JP | EP 0484800 A2 * | 5/1992 | ............... B01J 23/80 |
| WO | 9829374 A1 | 7/1998 | |
| WO | 2014067602 A1 | 5/2014 | |

OTHER PUBLICATIONS

International Preliminary Report on Patentability dated Apr. 30, 2015.
International Search Report dated Feb. 28, 2014.

* cited by examiner

*Primary Examiner* — Rosalynd Keys
*Assistant Examiner* — Kofi Adzamli
(74) *Attorney, Agent, or Firm* — Michael W. Ferrell

(57) ABSTRACT

A method for preparing neopentyl glycol by addition of isobutyraldehyde and formaldehyde in the presence of a tertiary alkylamine as catalyst to give hydroxypivalaldehyde with subsequent hydrogenation at a temperature of 80 to 140° C. and at a pressure of 2 to 18 MPa in the liquid phase, is characterized in that the hydrogenation is carried out in the presence of a copper chromite catalyst comprising the activators barium and manganese.

20 Claims, No Drawings

METHOD FOR THE PRODUCTION OF NEOPENTYL GLYCOL

CLAIM FOR PRIORITY

This application is a national phase application of PCT/EP2013/002922 FILED Sep. 28, 2013 which was based on application DE 10 2012 021 280.1 FILED Oct. 29, 2012. The priorities of PCT/EP2013/002922 and DE 10 2012 021 280.1 are hereby claimed and their disclosures incorporated herein by reference.

TECHNICAL FIELD

The present invention relates to a method for preparing neopentyl glycol by hydrogenation of hydroxypivalaldehyde in the liquid phase over barium- and manganese-doped copper chromite catalysts.

BACKGROUND

Polyhydric alcohols or polyols possess considerable economic significance as a condensation component for forming polyesters or polyurethanes, synthetic resin coatings, lubricants and plasticizers. In this context, polyhydric alcohols of interest are particularly those which are obtained by a mixed aldol addition of formaldehyde with iso- or n-butyraldehyde. The aldol addition between formaldehyde and the appropriate butyraldehyde first forms an aldehydic intermediate which then has to be reduced to the polyhydric alcohol. An industrially important polyhydric alcohol obtainable by this method is neopentyl glycol [NPG, 2,2-dimethylpropane-1,3-diol] formed from the mixed aldolization of formaldehyde and isobutyraldehyde.

The aldol addition is carried out in the presence of basic catalysts, for example, alkali metal hydroxides or aliphatic amines, and initially affords the isolable hydroxypivalaldehyde (HPA) intermediate. This intermediate can subsequently be converted with excess formaldehyde in accordance with the Cannizzaro reaction to neopentyl glycol to form one equivalent of a formate salt. In this configuration of the reduction step, the formate salt is therefore obtained as co-product and the cost-effectiveness of this method variant also depends on the commercial opportunities for the formate salt. However, also implemented industrially is the catalytic hydrogenation of hydroxypivalaldehyde in the gas and liquid phase over a metal catalyst. Suitable hydrogenation catalysts have been found, according to EP 0 278 106 A1, to be nickel catalysts. Catalysts based on copper, zinc and zirconium are used in the hydrogenation step in the method according to EP 0 484 800 A2.

Copper chromite catalysts are also frequently used for the hydrogenation of hydroxypivalaldehyde. Copper chromite catalysts frequently comprise other metals as activators, for example barium, cadmium, magnesium, manganese and/or a rare earth metal. According to U.S. Pat. No. 4,855,515, manganese-doped copper chromite catalysts in particular excel in the hydrogenation of the aldolization product of the reaction of formaldehyde with isobutyraldehyde. WO98/29374 A1 discloses the use of a barium-doped copper chromite catalyst for the hydrogenation of hydroxypivalaldehyde in a methanolic solution.

According to the teaching of DE 1 518 784 A1, a mixture of hydroxypivalaldehyde and excess isobutyraldehyde is hydrogenated to neopentyl glycol and isobutanol in the presence of a copper chromite catalyst which has been doped with barium. According to EP 0 006 460 A1, the two-step high pressure hydrogenation of crude hydroxypivalaldehyde, which is carried out with increasing hydrogenation temperatures, also uses a copper chromite catalyst activated with barium.

GB 2 482 887 A discloses the use of copper chromite catalysts, doped with both manganese and barium, for the hydrogenation of furfural. Distribution of product can be steered in the direction of furfuryl alcohol or 2-methylfuran, according to the choice of hydrogenation temperatures.

EP 0 301 853 A1 describes copper chromite catalysts which may include both barium and manganese as further adjuvants. The known catalysts can be used for the hydrogenation of aldehydes.

The copper chromite catalysts known from the prior art operate at comparatively high hydrogenation temperatures.

Copper chromite catalysts not only possess a good hydrogenation activity regarding conversion of hydroxypivalaldehyde to neopentyl glycol, but they are also sufficiently active so as to cleave by-products, which are formed during aldolization of isobutyraldehyde with formaldehyde, under hydrogenating conditions and to liberate neopentyl glycol bound to the by-products. Such by-products are, for example, neopentyl glycol isobutyrate or the Tishchenko ester, neopentyl glycol monohydroxypivalate, formed by the disproportionation of hydroxypivalaldehyde. The specific cleavage by hydrogenation of high-boiling by-products from the neopentyl glycol preparation using copper chromite catalysts is described in DE 10 2008 033163 A1.

EP 0 522 368 A1 discloses carrying out the hydrogenation of hydroxypivalaldehyde in a solution comprising at least 20% by weight of a low molecular weight alcohol, for example methanol or n-butanol, based on the mixture of alcohol and reaction product, and also water in an amount of not more than 40% by weight, based on the total amount of water, alcohol and reaction product. The hydrogenation catalyst recommended is a copper chromite catalyst.

As a product produced industrially, neopentyl glycol has a major economic significance and thus there always exists a need to improve the known methods for preparing neopentyl glycol, whether by improving the product yield, by better utilization of plant equipment or by a lowering of energy input.

SUMMARY OF INVENTION

It has surprisingly been found that neopentyl glycol may be prepared with high selectivity and high space time yield by hydrogenation of hydroxypivalaldehyde if the hydrogenation is conducted in the liquid phase in the presence of a copper chromite catalyst which has been doped both with manganese and with barium.

The present invention therefore relates to a method for preparing neopentyl glycol by addition of isobutyraldehyde and formaldehyde in the presence of a tertiary alkylamine as catalyst to give hydroxypivalaldehyde with subsequent hydrogenation at a temperature of 80 to 140° C. and at a pressure of 2 to 18 MPa in the liquid phase, characterized in that the hydrogenation is carried out in the presence of a copper chromite catalyst comprising the activators barium and manganese.

It has surprisingly been found that a complete hydrogenation of hydroxypivalaldehyde can be attained using copper chromite catalysts which comprise both barium and manganese as activators, even at distinctly lower temperatures, and very high space time yields can be achieved. The selective hydrogenation of hydroxypivalaldehyde to neopentyl glycol with high space time yields is successful by setting a hydrogenation temperature of 80 to 140° C., preferably 110 to 140° C. By using specifically doped copper chromite catalysts, in accordance with the invention, and by the precise selection of the hydrogenation temperature, the formation of high boilers during the hydrogenation reaction can also be suppressed, in comparison with a procedure in which conventional copper chromite catalysts are used and where a hydrogenation temperature of less than 80° C. is employed. At excessively low hydrogenation temperatures, hydroxypivalaldehyde is not completely hydrogenated. At excessively high hydrogenation temperatures an increased decomposition of the tertiary alkylamine used as the aldolization catalyst also occurs, which leads to secondary products that are difficult to remove and is therefore undesirable. The high boilers are oxygen-containing compounds such as esters or cyclic acetals in which equivalents of neopentyl glycol are chemically bound. In the high boilers, the proportion is particularly high of mono- and diisobutyric acid esters of neopentyl glycol and also of the neopentyl glycol monohydroxypivalate disproportionation product formed from hydroxypivalaldehyde by the Tishchenko reaction.

DETAILED DESCRIPTION

The aldol addition of isobutyraldehyde and an aqueous formaldehyde solution is conducted in the presence of tertiary alkylamines as aldol addition catalyst, which may comprise the same or different alkyl groups and therefore may be symmetrically or asymmetrically composed, or in the presence of tertiary alkylamines having a plurality of trialkylamine functions. The reaction is conducted in the presence of, for example, trimethyl-, triethyl-, tri-n-propyl-, triisopropyl-, methyldiethyl-, methyldiisopropylamine, tri-n-butylamine, dimethyl-tert-butylamine or N,N'-tetramethylethylenediamine. Trimethylamine, triethylamine, tri-n-propylamine and tri-n-butylamine have proven to be particularly suitable catalysts.

The aldehydes can be reacted in a molar ratio, but it is also possible to use one of the two reaction partners in excess. Formaldehyde is used in aqueous solution of which the aldehyde content is typically 20 to 50% by weight. It has been found that the doped copper chromite catalyst used in the method according to the invention has a surprisingly high resistance to formaldehyde. Thus, in the aldol addition stage, the molar ratios of formaldehyde to isobutyraldehyde of 1:1 can be adjusted in favour of formaldehyde, generally up to 1.2:1, preferably 1.1:1. By reducing the isobutyraldehyde input, the isobutanol formation in the hydrogenation stage is suppressed and the neopentyl glycol yield, based on isobutyraldehyde input, is increased.

The reaction between isobutyraldehyde and formaldehyde is conducted at temperatures between 20 and 100° C., advantageously from 80 to 95° C. Generally the reaction is carried out at standard pressure, but elevated pressure can also be used. The tertiary alkylamine used as the aldol addition catalyst is present in the reaction mixture in an amount of 1 to 20, preferably to 2 to 12 mol %, based on isobutyraldehyde.

In addition to the water from the aqueous formaldehyde solution and low amounts of methanol, which is also present in the aqueous formaldehyde solution, isobutanol is optionally added to the reaction mixture as diluent. The isobutanol addition is not strictly required, but, if isobutanol is added, the content in the reaction mixture is in the range of 10 to 20% by weight, based on the total reaction mixture. Additional solvents and diluents are not required.

The practical procedure for the addition reaction is conducted in a stirred tank, in a stirred tank cascade or in a reaction tube which may be charged with random packings or other internals to improve mixing of the reactants. The reaction proceeds exothermically and can be accelerated by heating.

The crude mixture arising from the aldol addition is hydrogenated catalytically in the presence of a barium- and manganese-doped copper chromite catalyst optionally following distillative removal of volatile components such as water, methanol, isobutanol and residual amounts of formaldehyde, isobutyraldehyde and optionally aldolization catalyst or without prior separation into its components or removal of individual components.

The hydrogenation is preferably carried out in the presence of an aliphatic alcohol which is miscible with the aldolization crude product. Suitable aliphatic alcohols have proven to be linear or branched alcohols having 1 to 5 carbon atoms such as methanol, ethanol, n-propanol, isopropanol, n-butanol, isobutanol, neopentyl glycol or mixtures thereof. Particularly advantageous is the use of isobutanol, since residual amounts of isobutyraldehyde are hydrogenated to isobutanol. If isobutanol is already added as diluent in the aldol addition step and is not removed beforehand by distillation, a solvent is already present in the hydrogenation step. Small amounts of methanol, which are incorporated in the aqueous formaldehyde solution, are also present. The proportion of aliphatic alcohol as organic solvent or diluents in this configuration of the invention is 15 to 27% by weight, preferably 15 to 23% by weight, based on the organic component in the starting mixture. By the addition of diluent or solvent a sufficient solubility of hydroxypivalaldehyde in the liquid phase during the hydrogenation stage is ensured and also the precipitation of hydroxypivalaldehyde is prevented and the homogeneity of the liquid phase ensured. If the alcohol content is too high valuable reactor volume is unnecessarily occupied and not fully utilized.

In a particularly preferred configuration of the method according to the invention, the liquid phase used for the hydrogenation also comprises water, in addition to the aliphatic alcohol, in an amount of 15 to 25% by weight, preferably 18 to 25% by weight, based on the total amount used. The overall starting mixture used for the hydrogenation is homogeneous and comprises therefore 15 to 25% by weight of water and, as remainder at 100% by weight, of an organic component which comprises in turn 15 to 27% by weight of an aliphatic alcohol.

The water component promotes advantageous heat distribution and advantageous dissipation of the heat of reaction during the hydrogenation step and reduces the danger of local temperature spikes occurring.

The crude mixture obtained containing hydroxypivalaldehyde is hydrogenated without further purification and work-up steps.

The hydrogenation of the crude hydroxypivalaldehyde is carried out in the liquid phase in the presence of barium- and manganese-doped copper chromite catalysts at a temperature of 80 to 140° C., preferably 110 to 140° C. The reaction pressure is 2 to 18 MPa, preferably 4 to 15 MPa. Of particular proven worth is a reaction temperature of 110 to 140° C. and a reaction pressure of 4 to 15 MPa. At lower reaction pressures, satisfactory hydrogenation of hydroxypivalaldeyhde is no longer observed.

The hydrogenation of hydroxypivalaldehyde is conducted in the presence of copper chromite catalysts which comprise barium and manganese as activators. Copper chromite catalysts may be described, according to H. Adkin, Org. React. 8, 1954, 1-27, as an equimolar combination of copper oxide and copper chromite, although they do not necessarily comprise copper chromite. Catalysts may be used either without carriers as unsupported catalysts or with carriers such as kieselguhr, silica gel or aluminium oxide as powders or in the form of tablets, stars, cylinders, rings or other particles of proportionately large surface area.

For the preparation, insoluble compounds of each of copper, chromium, manganese and barium are mixed, for example, in paste form and shaped into suitable bodies such as cylinders or tablets. After shaping, the latter are dried and calcined up to 500° C., wherein the solid compresses and the metals present are converted, if applicable, into the oxides.

It is also advantageous to start with aqueous solutions from which the solute is precipitated. Following filtration, the solid is dried and calcined up to 500° C., as with solid mixtures. Subsequently, it may be advisable to stir the solid in a low molecular weight organic acid such as formic acid, acetic acid, propionic acid or n-butyric acid in order to remove soluble constituents, then to wash until free of acid, to dry again and to calcine up to 500° C.

Following addition of additives such as graphite or alkali metal soaps or alkaline earth metal soaps, shaped bodies such as tablets or rings can then be produced.

The barium- and manganese-doped copper chromite catalysts comprise from 0.5 to 8% by weight, preferably from 3 to 5% by weight of manganese and from 0.5 to 8% by weight, preferably from 1 to 4% by weight of barium, based on the total content of copper, chromium, barium and manganese. Of particularly proven value is a barium content in a range from 1 to 4% by weight and a manganese content in a range from 3 to 5% by weight, in each case based on the total content of copper, chromium, barium and manganese. In addition to the activators mentioned, further activators such as cadmium, magnesium, strontium and/or a rare earth metal can optionally be present.

The hydrogenation is conducted in the liquid phase continuously or in batch mode, for example over solid catalysts arranged according to trickle mode or liquid phase mode and also according to suspension hydrogenation.

In the continuous fixed bed method, a catalyst hourly space velocity V/Vh, expressed in throughput volume per unit catalyst volume and time, of 0.2 to 4.0 $h^{-1}$, preferably 0.8 to 2.0 $h^{-1}$, has proven to be advantageous.

In the batchwise mode procedure, 1 to 20, preferably 2 to 15% by weight of copper chromite catalyst is used, based on the liquid starting product.

A higher hourly space velocity for the copper chromite catalyst is to be avoided since the hydroxypivalaldehyde starting compound is then no longer completely hydrogenated and an increased by-product formation is observed.

The hydrogenation is preferably carried out continuously in the liquid phase in a tubular reactor over fixedly arranged catalysts. A tubular reactor is also understood to mean a bundle of several narrow parallel connected tubes. The tubular reactors used may also comprise random packings or internals, for example Raschig rings, saddles, Pall rings, filter plates or column trays, and also optionally stirring devices or devices for dissipating the heat of reaction. In a particularly preferred configuration, the hydrogenation of hydroxypivalaldehyde is carried out in a tubular reactor on a fixed bed, but without internals and without stirring devices.

The hydrogenation is preferably carried out with pure hydrogen. However, it is also possible to use mixtures comprising free hydrogen and, in addition, constituents inert under the hydrogenation conditions.

The pure neopentyl glycol is obtained from the hydrogenated reaction mixture following conventional distillation methods. Solvents or diluents removed in this context may be fed back again into the aldol addition stage and/or hydrogenation stage.

The hydrogenation method according to the invention converts hydroxypivalaldehyde to neopentyl glycol with a high conversion, high selectivity and high space time yield. The low proportion of high boilers after hydrogenation is notable and the formation of high boilers in the hydrogenation stage can be effectively eliminated. The cleavage of the tertiary alkylamine into volatile, nitrogen-containing compounds, which lead to undesirable impurities and which are difficult to remove in the subsequent distillative work-up and which interfere during the further work-up of neopentyl glycol, is suppressed.

The method according to the invention is further illustrated by means of some examples which follow.

EXAMPLES

Example 1

Preparation of a Barium-Doped Copper Chromite Catalyst 28 g of copper nitrate trihydrate and 2.5 g of barium nitrate were dissolved in 200 ml of water at 55° C. Separately, 26 g of ammonium dichromate were dissolved in 120 ml of water and 40 ml of 25% ammonia solution. The ammonium dichromate solution was then slowly added dropwise to the copper nitrate solution. A red-brown solid precipitated. To complete the precipitation, the mixture was further stirred for one hour and cooled to room temperature. The solid was then filtered off and dried at 110° C. in a drying cabinet. The dried solid was calcined at 350° C. over 4 hours at a heating rate of 2° C./min. Following the calcination and cooling of the solid, it was stirred with 200 ml of 10% acetic acid. The solid was then washed free of acid with water and again dried at 110° C. and calcined at 350° C. at a heating rate of 2° C./min. The solid obtained in this form was used as catalyst. Based on the metals, the catalyst had the following composition: 42.1% copper, 48.4% chromium, 9.5% barium.

Example 2

Preparation of a Manganese-Doped Copper Chromite Catalyst 28 g of copper nitrate trihydrate and 5.0 g of manganese nitrate in the form of a 50% solution in dilute nitric acid was dissolved in 200 ml of water at 55° C. Separately, 26 g of ammonium dichromate were dissolved in 120 ml of water and 40 ml of 25% ammonia solution. The ammonium dichromate solution was then slowly added dropwise to the copper nitrate solution. A red-brown solid precipitated. To complete the precipitation, the mixture was further stirred for one hour and cooled to room temperature. The solid was then filtered off and dried at 110° C. in a drying cabinet. The dried solid was calcined at 350° C. over 4 hours at a heating rate of 2° C./min. Following the calcination and cooling of the solid, it was stirred with 200 ml of 10% acetic acid. The solid was then washed free of acid with water and again dried at 110° C. and calcined at 350° C. at a heating rate of 2° C./min. The solid obtained in this form was used as catalyst. Based on the metals, the catalyst had the following composition: 50.0% copper, 45.8% chromium, 4.2% manganese.

Example 3

Preparation of a Manganese- and Barium-Doped Copper Chromite Catalyst 2.8 kg of copper nitrate trihydrate, 400 g of manganese nitrate in the form of a 50% solution in dilute nitric acid and 150 g of barium nitrate were dissolved in 20 liters of water at 55° C. Separately, 2.6 kg of ammonium dichromate were dissolved in 12 liters of water and 4 liters of 25% ammonia solution. The ammonium dichromate solution was then slowly added dropwise to the copper nitrate solution. A red-brown solid precipitated. To complete the precipitation, the mixture was further stirred for one hour and cooled to room temperature. The solid was then filtered off and dried at 110° C. in a drying cabinet. The dried solid was calcined at 350° C. over 4 hours at a heating rate of 2° C./min. Following the calcination and cooling of the solid, it was stirred with 20 liters of 10% acetic acid. The solid was then washed free of acid with water and again dried at 110° C. and calcined at 350° C. at a heating rate of 2° C./min. The solid obtained in this form was used as catalyst. Based on the metals, the catalyst had the following composition: 47.5% copper, 46.5% chromium, 4.0% manganese, 2.0% barium.

Example 4

Comparison of the Catalytic Activity of the Catalysts from Examples 1-3

To test the catalytic activity of the copper chromite catalysts prepared according to examples 1-3, a crude hydroxypivalaldehyde solution was used which had been prepared by the aldol reaction of isobutyraldehyde with formaldehyde with tri-n-propylamine catalysis and had the following composition:

Organic component (determined gas chromatographically, data in percent):

| | |
|---|---|
| Formaldehyde | 1.4 |
| Isobutyraldehyde | 7.1 |
| Tri-n-propylamine | 10.3 |
| Isobutanol | 22.7 |
| Hydroxypivalaldehyde | 54.4 |
| Neopentyl glycol | 0.8 |
| Tishchenko ester | 3.3 |
| Water; in % by weight based on the total starting mixture | 22.4 |

Tishchenko ester: neopentyl glycol monohydroxypivalate

In each case, 10% by mass of the catalyst was used for hydrogenation of the crude hydroxypivalaldehyde solution.

The hydrogenation was carried out in an autoclave at 130° C. and at a hydrogen pressure of 8 MPa over 4 hours. The conversion was determined by means of the following formula:

Conversion (%)=((Amount of hydroxypivalaldehyde in the starting mixture−amount of hydroxypivalaldehyde after hydrogenation)/Amount of hydroxypivalaldehyde in the starting mixture)*100

The selectivity was determined by means of the following formula:

Selectivity (%)=(Amount of neopentyl glycol after hydrogenation/(Amount of hydroxypivalaldehyde in the starting mixture−amount of hydroxypivalaldehyde after hydrogenation))*100

The following result was obtained:

| | Catalyst from example | | |
|---|---|---|---|
| | 1 | 2 | 3 |
| Conversion (%) | 83.3 | 98.4 | 99.4 |
| Selectivity (%) | 91.2 | 94.5 | 94.0 |

Example 5

Influence of the Tertiary Amine on the Hydrogenation Activity

10% by mass of the catalyst from example 3 was used for hydrogenating crude hydroxypivalaldehyde of the following composition:

| | |
|---|---|
| Formaldehyde | 1.3 |
| Isobutyraldehyde | 22.0 |
| Isobutanol | 22.5 |
| Hydroxypivalaldehyde | 47.1 |
| Neopentyl glycol | 5.0 |
| Tishchenko ester | 2.1 |
| Water; in % by weight based on the total starting mixture | 20.3 |

The hydrogenation was conducted in an autoclave at 130° C. and at a hydrogen pressure of 8 MPa over 4 hours.

The following result was obtained:

| | |
|---|---|
| Conversion (%) | 98.0 |
| Selectivity (%) | 77.9 |

The values for the conversion and particularly the selectivity from example 5 and from example 4/catalyst 3 show that the presence of the tertiary amine in the crude hydroxypivalaldehyde has a beneficial effect on the hydrogenation properties of the barium- and manganese-doped copper chromite catalyst.

Example 6

Use of the Catalyst from Example 3 as Fixed Bed Catalyst

The catalyst from example 3 was mixed with 3% graphite and tabletted. The 3×3 mm tablets were placed in a 2.2 liter volume tubular reactor. The catalyst was then activated at 240° C. for 5 hours in a gas stream containing 15 mol % hydrogen and 85 mol % nitrogen at atmospheric pressure. This gas mixture was passed over the catalyst at 200 normal l/h. 1 Normal liter means 1 liter gas volume at a temperature of 20° C. and a pressure of 0.1 MPa. Crude hydroxypivalaldehyde, corresponding to the composition according to example 4, and hydrogen were continuously fed into the bottom of the tubular reactor. The hydrogenation material was removed from the top of the tubular reactor, piped into a high-pressure separator and hence fed into a non-pressurized vessel via a level control. The hydrogenation temperature and the catalyst hourly space velocity were adjusted according to the conditions in Table 1 below. The hydrogen pressure was adjusted to 8 MPa in all experiments.

TABLE 1

Continuous liquid phase hydrogenation of hydroxypivalaldehyde over manganese- and barium-doped copper chromite catalyst according to example 3

| Temperature/° C. | V/Vh/h$^{-1}$ | Hydroxypivalaldehyde conversion/% | Selectivity for neopentyl glycol/% |
|---|---|---|---|
| 155 | 3.00 | 99.7 | 98.9 |
| 145 | 2.00 | 99.8 | 98.9 |
| 135 | 1.75 | 99.9 | 100 |
| 120 | 1.20 | 99.9 | 100 |

The results in Table 1 show that excellent conversion and selectivity values and therefore space time yields can be observed at hydrogenation temperatures of 120 to 135° C. even at comparatively high catalyst hourly space velocities of 1.2 to 1.75 liters of hydrogenation feed per liter of catalyst per hour. At still higher temperatures and catalyst hourly space velocities, a virtually complete conversion is likewise achieved, although the selectivity for neopentyl glycol decreases. Under these experimental conditions, which are no longer entirely optimal, increased cleavage reactions of the tertiary amines used as aldolization catalysts should also be expected.

Example 7 Comparative Example

A commercial supported nickel catalyst in the form of 3×3 mm tablets was placed in a 2.2 liter volume tubular reactor. Crude hydroxypivalaldehyde, corresponding to the composition according to example 4, and hydrogen were continuously fed into the bottom of the tubular reactor. The hydrogenation material was removed from the top of the tubular reactor, piped into a high-pressure separator and hence fed into a non-pressurized vessel via a level control. The hydrogenation temperature and the catalyst hourly space velocity were adjusted according to the conditions in Table 2 below. The hydrogen pressure was adjusted to 8 MPa in all experiments.

TABLE 2

Continuous liquid phase hydrogenation of hydroxypivalaldehyde over a nickel catalyst

| Temperature/° C. | V/Vh/h$^{-1}$ | Hydroxypivalaldehyde conversion/% | Selectivity for neopentyl glycol/% |
|---|---|---|---|
| 130 | 0.27 | 99.9 | 96.5 |
| 130 | 0.53 | 99.9 | 97.3 |
| 130 | 0.90 | 98.2 | 99.1 |

The results in Table 2 show that only a distinctly lower space time yield could be achieved over a nickel catalyst than over the catalyst from example 3. Moreover, the selectivity for neopentyl glycol is lower over the nickel catalyst than over the catalyst from example 3.

The invention claimed is:

1. Method for preparing neopentyl glycol by addition of isobutyraldehyde and formaldehyde in the presence of a tertiary alkylamine as catalyst to give hydroxypivalaldehyde with subsequent hydrogenation at a temperature of 80 to 140° C. and at a pressure of 2 to 18 MPa in the liquid phase, characterized in that the hydrogenation is carried out in the presence of a copper chromite catalyst comprising the activators barium and manganese.

2. Method according to claim 1, characterized in that the hydrogenation is carried out in the presence of an aliphatic alcohol in an amount of 15 to 27% by weight, based on the organic component in the starting mixture.

3. Method according to claim 1, characterized in that the hydrogenation is carried out at a temperature of 110 to 140° C. and at a pressure of 4 to 15 MPa.

4. Method according to claim 1, characterized in that the tertiary alkylamines used are symmetrical tertiary alkylamines.

5. Method according to claim 4, characterized in that the symmetrical tertiary alkylamines used are trimethylamine, triethylamine, tri-n-propylamine or tri-n-butylamine.

6. Method according to claim 1, characterized in that the tertiary alkylamines used are asymmetrical tertiary alkylamines or compounds having a plurality of trialkylamine functions.

7. Method according to claim 2, characterized in that the aliphatic alcohols used are linear or branched alcohols having 1 to 5 carbon atoms.

8. Method according to claim 7, characterized in that methanol, ethanol, n-propanol, isopropanol, n-butanol, isobutanol, neopentyl glycol or mixtures thereof are used.

9. Method according to one or more of claim 1, characterized in that the copper chromite catalyst comprises barium in an amount of 0.5 to 8% by weight and manganese in an amount of 0.5 to 8% by weight, in each case based on the total content of copper, chromium, barium and manganese.

10. Method according to claim 9, characterized in that the copper chromite catalyst comprises barium in an amount of 1 to 4% by weight and manganese in an amount of 3 to 5% by weight, in each case based on the total content of copper, chromium, barium and manganese.

11. Method according to claim 2, characterized in that the liquid phase used for the hydrogenation comprises water in an amount of more than 15 to 25% by weight based on the total amount used.

12. Method according to one or more of claim 1, characterized in that the hydrogenation is carried out in a tubular reactor without internals and without stirring devices.

13. Method according to claim 2, characterized in that the hydrogenation is carried out at a temperature of 110 to 140° C. and at a pressure of 4 to 15 MPa.

14. Method according to claim 2, characterized in that the tertiary alkylamines used are symmetrical tertiary alkylamines.

15. Method according to claim 3, characterized in that the tertiary alkylamines used are symmetrical tertiary alkylamines.

16. Method according to claim 14, characterized in that the symmetrical tertiary alkylamines used are trimethylamine, triethylamine, tri-n-propylamine or tri-n-butylamine.

17. Method according to claim 15, characterized in that the symmetrical tertiary alkylamines used are trimethylamine, triethylamine, tri-n-propylamine or tri-n-butylamine.

18. Method according to claim 2, characterized in that the tertiary alkylamines used are asymmetrical tertiary alkylamines or compounds having a plurality of trialkylamine functions.

19. Method according to claim 3, characterized in that the tertiary alkylamines used are asymmetrical tertiary alkylamines or compounds having a plurality of trialkylamine functions.

20. Method according to claim 3, characterized in that the aliphatic alcohols used are linear or branched alcohols having 1 to 5 carbon atoms.

* * * * *